United States Patent [19]

Larkin

[11] Patent Number: 4,781,679

[45] Date of Patent: Nov. 1, 1988

[54] CONTAINER SYSTEM WITH INTEGRAL SECOND SUBSTANCE STORING AND DISPENSING MEANS

[75] Inventor: Mark E. Larkin, Lindenhurst, Ill.

[73] Assignee: Abbott Laboratories, North Chicago, Ill.

[21] Appl. No.: 873,665

[22] Filed: Jun. 12, 1986

[51] Int. Cl.[4] ............................................ A61M 37/00

[52] U.S. Cl. ...................................... 604/88; 604/413; 604/416

[58] Field of Search ................................... 604/82–92, 604/414–416, 413

[56] References Cited

U.S. PATENT DOCUMENTS

| | | | |
|---|---|---|---|
| 2,176,923 | 10/1935 | Nitardy | 206/221 |
| 2,590,900 | 4/1951 | Sommerstein | 604/415 |
| 2,721,552 | 10/1956 | Nosik | 206/222 |
| 2,778,360 | 1/1957 | Miskel | 128/218 |
| 3,290,017 | 12/1958 | Davies | 206/220 |
| 3,306,563 | 2/1967 | Soto | 206/219 |
| 3,532,254 | 10/1969 | Burke | 206/219 |
| 3,570,486 | 3/1969 | Engelsher | 604/88 |
| 3,636,950 | 1/1970 | Gomez | 128/218 M |
| 3,840,136 | 10/1974 | Lanfranconi et al. | 206/222 |
| 3,875,012 | 4/1975 | Dorn et al. | 206/222 |
| 3,915,212 | 10/1975 | Bujan et al. | 604/415 |
| 3,968,872 | 7/1976 | Cavazza | 604/416 |
| 4,048,999 | 9/1979 | Kobel | 604/90 |
| 4,059,112 | 11/1979 | Tischlinger | 604/413 |
| 4,089,432 | 5/1979 | Crankshaw et al. | 604/416 |
| 4,161,178 | 7/1980 | Genese | 128/272.3 |
| 4,169,475 | 10/1981 | Genese | 604/414 |
| 4,172,457 | 10/1981 | Choksi et al. | 604/416 |
| 4,187,893 | 2/1981 | Bujan | 604/415 |
| 4,289,648 | 9/1981 | Hoskins et al. | 604/416 |
| 4,294,351 | 10/1981 | Cheetham | 206/222 |
| 4,306,554 | 12/1983 | Schwartz et al. | 128/218 M |
| 4,392,850 | 7/1983 | Elias et al. | 604/416 |
| 4,397,442 | 8/1983 | Larkin | 251/342 |
| 4,405,317 | 9/1983 | Case | 604/90 |
| 4,412,836 | 11/1983 | Brignola | 604/87 |
| 4,417,890 | 11/1983 | Dennehey et al. | 604/256 |
| 4,467,588 | 8/1984 | Carveth | 206/219 |
| 4,515,586 | 5/1985 | Mendenhall et al. | 604/416 |
| 4,550,825 | 11/1985 | Sutryn | 206/222 |
| 4,583,971 | 4/1986 | Bocquet et al. | 604/82 |
| 4,589,879 | 5/1986 | Pearson | 604/88 |
| 4,601,704 | 7/1986 | Larkin | 604/416 |
| 4,606,734 | 8/1986 | Larkin et al. | 604/414 |
| 4,614,267 | 9/1986 | Larkin | 604/415 |

OTHER PUBLICATIONS

The Versatile, Complete Abbott Small Volume Parenteral System Abbott Laboratories, Mar. 1982.

*Primary Examiner*—C. Fred Rosenbaum
*Assistant Examiner*—Mark O. Polutta
*Attorney, Agent, or Firm*—Robert W. Stevenson; Michael J. Roth; Martin L. Katz

[57] ABSTRACT

The invention is an integral container system designed for separately storing a liquid, such as a diluent, and a second substance, such as a medicament, and subsequently adding the second substance to the liquid in a simple and sterile operation. In one embodiment, a flexible I.V. bag is provided with a second substance dispensing cup containing a powdered medicament, which cup fits slidably in a sleeve passing through the walls of the bag. Fitted in the open end of the cup is a pierceable plunger. A hollow needle is held in position to pierce the plunger when the cup is pushed toward the needle. The needle is slidably held so that when it is pushed by the plunger, it will also pierce a diaphragm fitting over the sleeve. When both the plunger and the diaphragm are pierced, fluid access between the cup and the bag is had through the hollow needle. Diluent can then be injected into the cup to dissolve or slurry the powdered medicament. When the cup is pushed further toward the bag, the plunger is stopped and the medicament is expelled from the cup as the volume is reduced.

22 Claims, 2 Drawing Sheets

FIG. 2
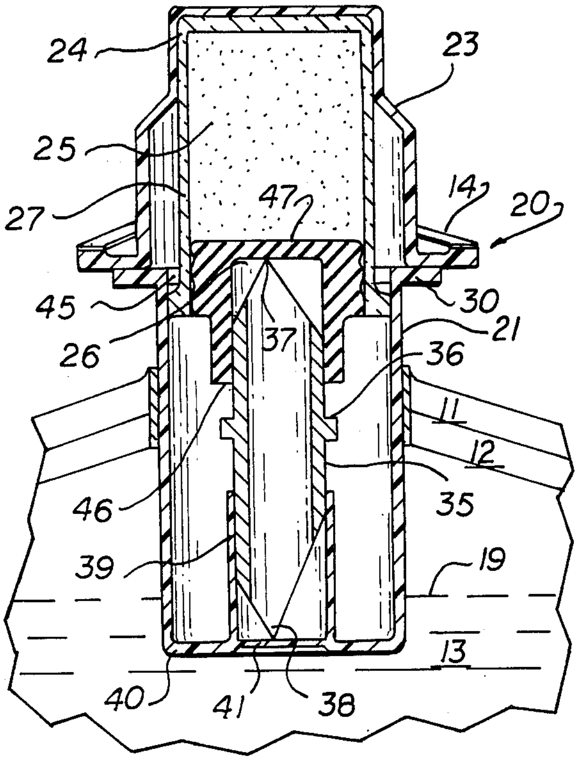
FIG. 2A
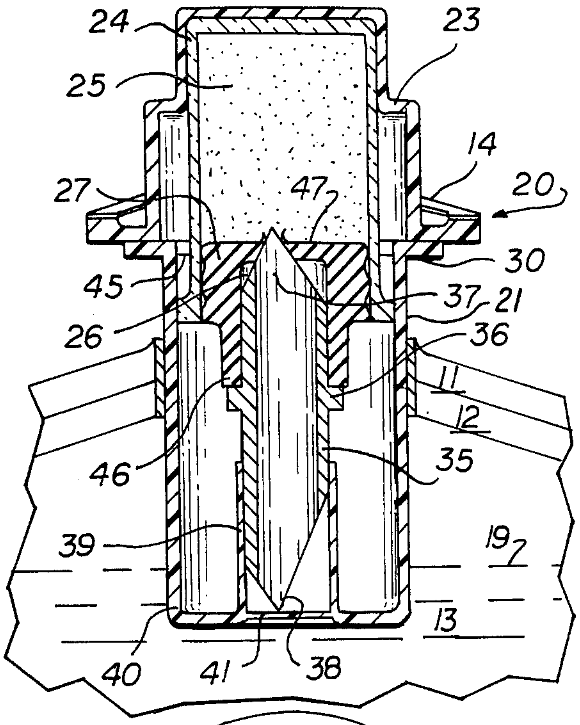
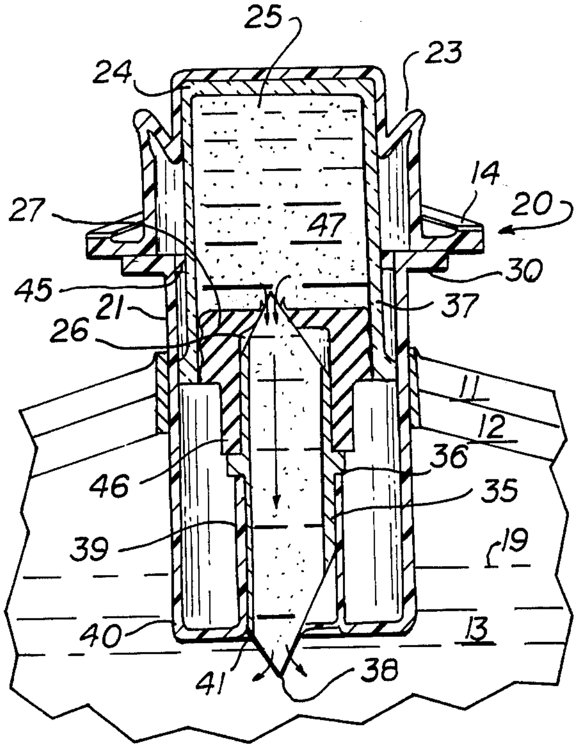
FIG. 2B
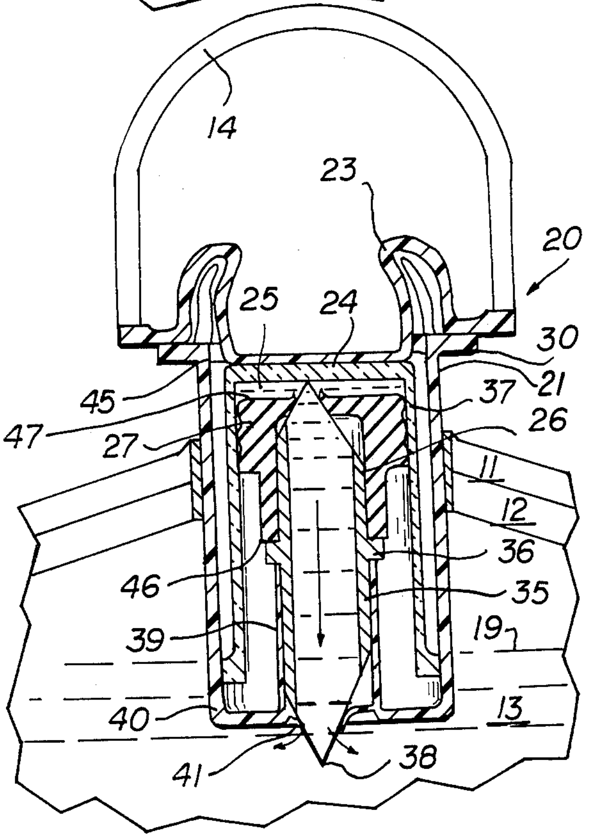
FIG. 2C

CONTAINER SYSTEM WITH INTEGRAL SECOND SUBSTANCE STORING AND DISPENSING MEANS

BACKGROUND OF THE INVENTION

This invention relates generally to container systems for the storing and delivering of liquids. More particularly, this invention relates to integral container systems such as flexible I.V. bags which have the capacity to separately store and subsequently dispense a second substance such as a medicament into a liquid diluent before delivery of the solution to its end use. As will be seen, the present invention exhibits particular utility in the pharmaceutical field. Accordingly much of the discussion herein relates to the pharmaceutical applications, particularly flexible I.V. bags. However, it should be noted that the present invention is not limited to these as other applications in which it provides advantages will become apparent to those skilled in the art. For example, the present invention may prove useful in the handling of photographic chemicals or analytical laboratory solutions, etc.

Container systems which can hold separately two components and subsequently mix those components are especially beneficial in the pharmaceutical field when working with a medicament which is reactive or relatively unstable when mixed with its intended diluent. For example, certain antibiotics have a useful life of only 6 to 12 hours after being mixed with their diluent for intravenous administration. In light of this, a hospital pharmacy is often required to keep a medicament and its diluent in completely separate containers and then to use some independent means for transferring one into the other just prior to delivery. A common practice is to keep the medicament in a glass vial with a pierceable stopper, to draw the medicament out with a cannula and syringe, and to use the cannula and syringe to inject the medicament into the container of the diluent just prior to delivery to the patient. Naturally, this method is tedious and introduces opportunities for error, contamination, and undue delay. Also, transferring by cannula and syringe is not feasible unless the medicament is in liquid form. As a result, when transferring a powdered medicament in this way, it is first necessary to inject a quantity of diluent into the vial to dissolve the powder thereby adding one more step to the process and adding one more possible source of contamination and error.

Another factor present in the pharmaceutical field is that one is required by chemical considerations and by law to store medicaments for long periods of time only in containers made by specified materials. Although glass and rubber are approved for a wide variety of medicaments, particular plastics have received government approval to be used in containers for only a limited number of medicaments. This is unfortunate because these plastics have proven superior to glass in storing and delivering intravenous liquids. In particular, the plastic flexible I.V. bag is often easier to fabricate, fill, and use—all the while maintaining sterility—than the glass I.V. bottle.

Some containers have previously been developed for storing different components separately so they can be intermixed later. However, an effective seal is often not maintained in such containers between the two components to be intermixed particularly in the face of the rigors of handling and shipping. Additionally, containers used in pharmaceutical applications must be completely sterile. Although relatively simple in configuration, the arrangement of parts in some containers makes them difficult to sterilize unless the entire device is assembled in a totally sterile environment. Such manufacture is tremendously expensive. Furthermore, none of these devices use different materials for contacting each of the components.

SUMMARY OF THE INVENTION

The invention is an integral container system which is designed for separately storing a liquid such as a diluent and a second substance such as a medicament. The container system also includes a means by which the second substance is mixed with the liquid. This result is achieved by providing a flexible container, such as an I.V. bag, which contains the liquid in its internal cavity. A means is also provided for storing and subsequently dispensing the second substance. This dispensing means includes a cup for holding the second substance. A plunger with a pierceable portion is snugly yet slidably fit within the open end of the cup. A hollow pin is provided which is held in position so that when the cup is pushed toward it, the plunger is pierced thereby providing fluid access between the hollow needle and the contents of the cup. As the cup is pushed further, the plunger is stopped and thereby continued pushing of the cup expels the contents of the cup through the needle and into the bag's cavity.

The dispensing means also includes a sleeve which passes through the walls of the container. The open end of the cup fits snugly yet slidably within the end of the sleeve disposed outside of the container and is adapted to be pushed through the sleeve toward the container. Located at the end of the sleeve which communicates with the internal cavity is a pierceable diaphragm. When the plunger and diaphragm are pierced, fluid access is had through the hollow needle between the contents of the cup and the internal cavity. This fluid access allows some of the liquid from the container to be injected into the cup. Also, as the cup is pushed further, the plunger's movement is stopped whereby continued pushing of the cup reduces the volume between the plunger and the cup. As a result the contents of the cup are positively expelled through the hollow pin into the internal cavity of the container. To avoid contamination, a collapsable cap closes the exterior end of the sleeve, sealing the cap within the sleeve and preventing touch contamination of the important parts of the system.

It will be appreciated that dispensing of the medicament into the diluent is accomplished in a relatively simple manner and with no possible source of contamination. In particular, neither the diluent nor the medicament are exposed to the air or any surfaces which were not sterilized at the time of manufacturing or filling the bag. This is important, particularly when dealing with pharmaceutical applications.

A further advantage is that the medicament or other substance is held in an integral container system with its intended diluent. The possibility of mixing the medicament with the wrong diluent is eliminated.

BRIEF DESCRIPTION OF THE DRAWINGS

A better understanding of the container system with an integral second substance storing and dispensing means will be had by reference to the accompanying drawings wherein:

FIG. 2 is a vertical partial cross-section of the dispensing means taken along line 2—2 of FIG. 1.

FIGS. 2A-2C are views similar to FIG. 2, which show the configuration and position of various elements of the dispensing means at sequential stages of its operation.

DETAILED DESCRIPTION

Figure 1:
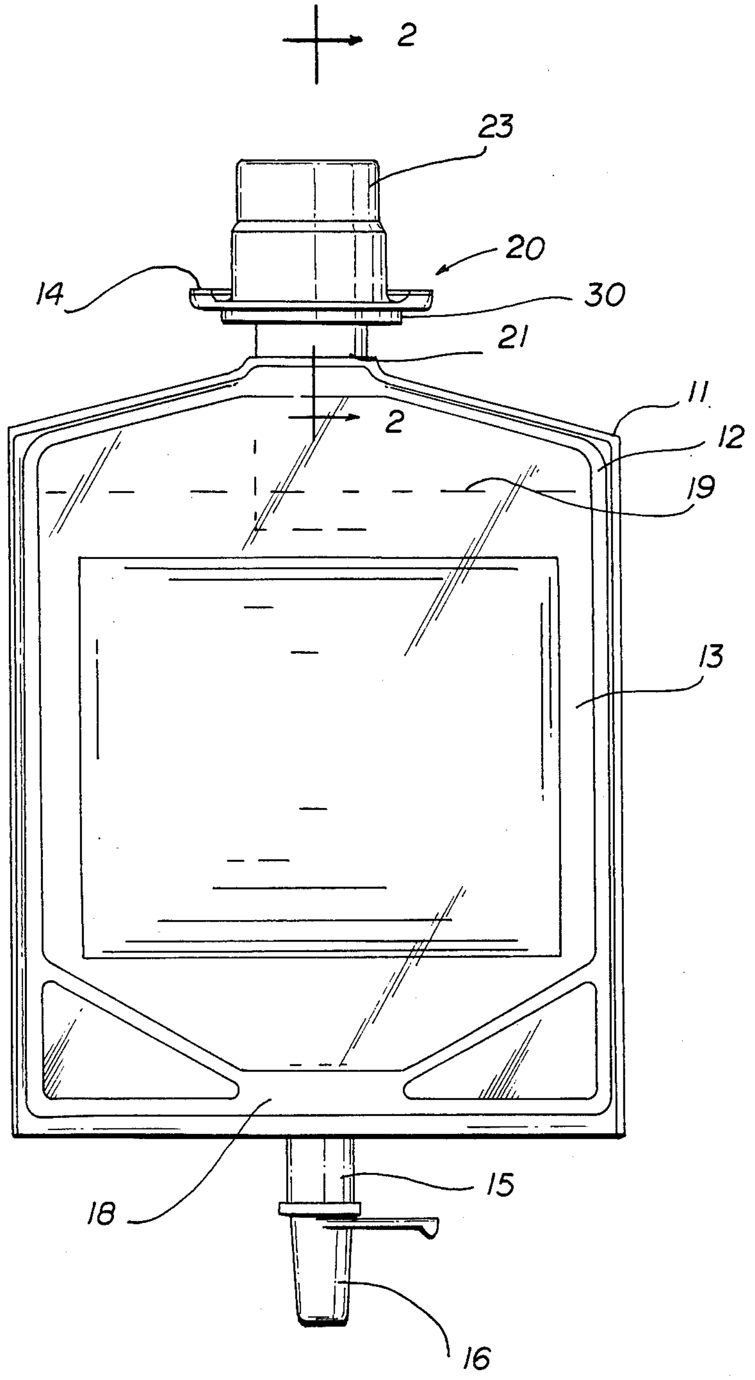
FIG. 1 is a view in front elevation of a container system of the present invention.

The container 10 (FIG. 1) in this preferred embodiment is a flexible bag for intravenous administration, commonly called an I.V. bag. The I.V. bag has two flexible wall members 11, preferably formed from a plastic such as polyvinylchloride, and which are joined near their periphery by a seal 12, thus creating an internal cavity 13 for containing the diluent 19 such as saline solution, dextrose solution, or water. Some air or other gas is often included within the internal cavity 13 of the bag 10. This keeps the bag from collapsing when most of the solution has been delivered. Extending through the bottom edge 18 of bag 10 and sealed by means of a mandrel-type seal is a tubular administration port 15 with a protective cap 16.

Dispensing means 20 is located at the top of the bag 10 and comprises a sleeve 21 which passes through and is sealed to the wall members 11. The bottom end of the sleeve 21 is disposed below the diluent level. Covering the upper portion of dispensing means 20 is a collapsible cap 23. Sleeve 21 includes a flanged end 30 for gripping with the index and middle fingers as the collapsible cap is pushed on by the thumb. In an alternative embodiment, the dispensing means is located at the bottom of the I.V. bag and passes through the bottom edge of the bag.

Referring again to the preferred embodiment shown, a hanging member 14 is hingedly attached to dispensing means 20. In particular, hanging member 14 includes an aperture for receiving a supporting hook to hang the bag 10 during use. In addition, hanging member 14 is positioned and sized so that it can swing into a substantially vertical position for hanging bag 10 only after the dispensing means has been activated. This is intended as a safety feature to insure that the medicament is added to the diluent before delivery to the patient.

As another safety feature, the collapsible cap 23 is made from a plastic which will crumple when pushed, providing a visual indicator of whether the medicament has been added. Also, it may be desirable to include an additional cap over the upper portion of the dispensing means 20 which is not collapsible whereby to prevent premature mixing of the diluent. Such a protective cap (not shown) could be threaded on, or equipped with a tearable feature which would allow it to be easily removed. Still another safety feature is provided by forming the sleeve 21 from a transparent material thus allowing the user to see if the medicament is in the dispensing means 20.

FIG. 2 is a cross-sectional view showing the dispensing means 20 in greater detail. Under collapsible cap 23 is a generally cylindrical cup 24 which contains a plurality of medicament 25. Cup 24 is preferably made of glass. The medicament 25 pictured here is in powdered form. As will be explained below, the present invention provides particular advantages when working with powdered medicaments. However, it should be noted that this invention is also well suited for a liquid medicament.

The open end of the cup 24 is flanged and fits snugly yet slidably within the sleeve 21. A washer 45 is also provided to stabilize the cup 24 as it is pushed through the sleeve 21. A plunger 27, preferably made of rubber, fits snugly yet slidably within the open end of the cup 24. The plunger includes a plunger sleeve 26 with an end portion 46 and a pierceable portion 47. The pierceable portion 47 communicates with the cavity of cup 24 on one side and with plunger sleeve 26 on its other side.

The sleeve 21 includes a bottom portion 40 to which is attached guiding means for a hollow piercing means in the form of a pin 35, which guiding means in this case is an upstanding cylindrical post 39. The post 39 is coaxial with the main portion of the sleeve 21 and includes a pierceable diaphragm 41 across its lower end 15. Diaphragm 41 communicates with the diluent 19 in the cavity 13 on one side and with the post 39 on the other.

The hollow needle or pin 35 fits slidably within both the cylindrical post 39 and the plunger sleeve 26. The piercing pin 35 includes a sharp point 37 at its upper end and another sharp point 38 at its lower end. In addition, the piercing pin 35 includes an annular external shoulder 36 intermediate its ends.

As cap 23 is pushed down and collapsed (FIG. 2A), cup 24 moves downwardly through the sleeve 21. Plunger 27 moves down with cup 24 and is thereby pushed against the sharp end 37 of the hollow pin 35 and the pierceable portion 47 is pierced. Also, the bottom end 46 of the plunger sleeve 26 has been brought into contact with the shoulder 36 of the pin 35. As a result, when the plunger 27 is pushed downwardly toward the pierceable diaphragm 41, the hollow pin 36 will also pierce the diaphragm 41.

Alternatively, the pierceable portion 47 may resist piercing enough that the pin 35 is pushed downwardly and through the pierceable diaphragm 41 before the pierceable portion 47 is pierced. In that event, shoulder 36 of the piercing pin 35 will be stopped by the top edge of the post 39 and continued pushing of the cup 24 will pierce the pierceable portion 47 of the plunger 27. At present, the order in which the plunger diaphragm 47 and the post diaphragm 41 are pierced is not deemed important. However, if for whatever reason, it is desired to pierce one before the other, that provision can be made by selecting the material and thickness of the two diaphragms 41 and 47 so that one or the other is more easily pierceable. Likewise, the friction between the pin or needle 35 and the plunger sleeve 26 or between the needle 35 and the post 39 can be tailored so that one or the other is pierced first.

When the bottom sharp end 38 of the pin or needle 35 is pushed through the diaphragm 41 (FIG. 2B), there is fluid access between the contents of the cup 24 and the internal cavity 13 of the bag 10. Because medicament 25 shown in this embodiment is a powder, it is recommended that the bag 10 be squeezed at this point. Because the bottom end of sleeve 21 is below the diluent level, diluent is thereby forced up through the hollow needle 35 and into cup 24. In this way, powdered medicament 25 is either dissolved or made into a slurry with the diluent whereby some may exit cup 24 through needle 35 for mixing with the remainder of diluent 19 in bag 10. In the alternative embodiment wherein dispensing means 29 is located at the bottom of bag 10, the squeezing of bag 10 may be unnecessary.

When the lower end 38 of the pin 35 is pushed through diaphragm 41, the shoulder 36 thereon has come into contact with the top of post 39. As a result, the pin or needle 35 and the plunger 27 are prevented from moving any further in a downward direction.

As the cap 23 and cup 24 are pushed further down (FIG. 2C), the contents of the cup, i.e., the medicament 25 and any diluent 19 in the cup 24, are positively expelled from the cup 24 through the hollow needle 35 and into the cavity 13 of the bag 10. In particular, since plunger 27 has been prevented from moving further downwardly because of shoulder 36 abutting the top of the post 39; when the cup 24 is pushed further downwardly, the volume is reduced and the contents are pushed out through the hollow pin or needle 35. An advantage of using a flexible bag 10 is that, if powder 25 is not readily dissolved, the bag can be squeezed and manipulated to cause more rapid dissolution. Likewise, if there is some medicament 25 remaining in cup 24, the bag can be squeezed to "wash" the cup.

FIG. 2C also shows that when cap 23 has been pushed all the way down, the hanging member 14 is now able to swing up into position for hanging the bag for use.

It will thus be seen that through the present invention there is now afforded an integral container system for delivering a mixture of first and second substances in which the second substance can be separately stored and subsequently dispensed into the first substance prior to delivery of the mixture. This dispensing operation is accomplished in a simple and positive manner and without opportunity for contamination or error. In addition, with the container system of this invention it is possible to provide a compartment for storing the medicament which comprises glass and rubber surfaces contacting the medicament, while at the same time providing the convenience of using a flexible plastic I.V. bag for delivering the solution. Because of these features, this container system is particularly advantageous in pharmaceutical applications when dealing with the requirement of storing and mixing a medicament and diluent for intravenous administration. However, as noted above, the present invention is not limited to this specific pharmaceutical application. Instead, it extends to the other applications, such as the handling of photographic chemicals, analytical solutions for laboratory use, etc. in which it is likewise advantageous to separately store and subsequently mix components in an integral container system.

Likewise, the invention exhibits particular advantages when working with a powdered material as the second substance. However, it should be noted that the invention also works well with a liquid as the second substance.

The present invention can now be practiced by those skilled in the art. The embodiments presented herein are intended as exemplary and not limiting. The scope of the present invention is to be defined by the terms of the following claims as given meaning by the preceding description.

I claim:

1. A container system for separately storing a liquid and a second substance and subsequently dispensing a mixture of the two substances comprising:

container means for containing and delivering a liquid, said container means having walls defining an internal cavity;

sleeve means mounted in a wall of said container, said sleeve means having a pierceable member closing one end thereof;

cup means for containing the second substance, said cup means being slideably positioned in said sleeve means, said cup means having an open end;

pierceable plunger means slideably positioned within said open end of said cup means;

collapsible cap means positioned over the other end of said sleeve means, and over said cup means; and hollow piercing means disposed between said pierceable plunger and said pierceable member; whereby as said cup means is urged toward said pierceable member by collapsing said cap means, said piercing means will pierce both said plunger means and said pierceable member, and said plunger means will be forced inwardly of said cup means so as to force said second material from said cup means through said hollow piercing means into said container means.

2. The container system of claim 1 wherein said container is a flexible I.V. bag.

3. The container system of claim 1 wherein said collapsible cap means is positioned at the top of the container and includes a hanging means from which the container system may be suspended during use.

4. The container system of claim 1 wherein said piercing means is in the form of a hollow pin and wherein said cup means is disposed initially at the other end of said sleeve whereby slideable displacement of said cup means toward said pierceable member will force said pin to pierce both said plunger pierceable portion and said pierceable member whereby to establish a path between said cup means and said container means through said hollow pin.

5. The container system of claim 4 wherein said sleeve includes an upstanding coaxial cylindrical post, a portion of said pin being supported by said post.

6. The container system as recited in claim 1 wherein said sleeve means includes a diaphragm sealingly closing said one end of said sleeve means, and said pierceable member comprises a reduced thickness portion of said diaphragm.

7. The container system as recited in claim 1 wherein said plunger means includes a tubular recess, at least a portion of said piercing means being supported within said tubular recess.

8. The container system as recited in claim 7 wherein said plunger means includes a pierceable portion within said tubular recess.

9. A container system for separately storing a liquid and a second substance and subsequently dispensing the second substance into the liquid comprising:

container means for containing and delivering a liquid having wall means defining an internal cavity;

sleeve means passing through the wall means having a first closed pierceable and extending into said internal cavity, and a second end disposed outside of the container;

cup means for containing a quantity of the second substance, said cup means being closed at one end and open at the other end, said open end fitting snugly and slideably within said second end of said sleeve means;

collapsible cap means sealingly closing said second end of said sleeve and thereby enclosing said cup means within said cap means and sleeve means;

plunger means fitting snugly and slideably within the open end of the cup means, and having a pierceable portion; and hollow piercing means positioned such that, when the cup means is pushed into the sleeve toward said first end of said sleeve and the plunger means is thereby pushed in the same direction, said piercing means pierces both said pierceable portion and said pierceable end thereby providing fluid access between said container means and the cup means.

10. The container system of claim 9 wherein said container is a flexible I.V. bag.

11. The container system of claim 9 wherein said collapsible cap means is provided with hanging means from which the container system may be suspended during use.

12. The container system of claim 11 wherein the hanging means is configured so as to be operable only after the second substance has been dispensed into the liquid.

13. The container system of claim 9 wherein the cup means is comprised of glass and the plunger means is comprised of rubber.

14. The container system of claim 9 wherein said hollow piercing means comprises a hollow pin; and said first pierceable end includes a pierceable diaphragm and guiding means for slideably supporting said hollow pin whereby when said hollow pin is pushed by the plunger means within said guiding means toward the first end of the sleeve means, it pierces said pierceable end of said sleeve means thereby providing fluid access between the hollow pin and the internal cavity.

15. The container system of claim 14 wherein said container is a flexible I.V. bag.

16. The container system of claim 14 wherein the cup means is comprised of glass and the plunger means is comprised of rubber.

17. An I.V. bag system for separately storing a medicament and a diluent and for subsequently mixing the medicament with the diluent prior to delivery, said system comprising:

a container for storing the diluent and for delivery of the mixed diluent and medicament, said container having wall means defining an internal cavity;

sleeve means passing through the wall means whereby a first pierceable end of the sleeve means communicates with the internal cavity and the second end is disposed outside of said container;

cup means for containing a quantity of the medicament, said cup means being closed at one end and open at the other end, said open end fitting snugly and slideably within the second end of the sleeve means;

plunger means fitting snugly and slideably within the open end of the cup means, and having a pierceable portion;

a hollow pin with a first sharp end disposed such that, when the cup means is pushed into the sleeve means toward said first end of said sleeve means and the plunger means is thereby pushed in the same direction, said first sharp end pierces said pierceable portion thereby providing fluid access between the hollow pin and the cup means;

a pierceable diaphragm positioned at said first end of said sleeve means, and guiding means in said sleeve means for slideably holding said hollow pin whereby when the hollow pin is pushed by the plunger means within said guiding means toward the first end of the sleeve means, a second sharp end thereon pierces the diaphragm of said sleeve means thereby providing fluid access between the hollow pin and the internal cavity.

18. The I.V. bag system of claim 17 wherein said container is a flexible I.V. bag.

19. The I.V. bag system of claim 17 further comprising a collapsible cap means positioned over said cup means.

20. The I.V. bag system of claim 19 wherein said sleeve means is positioned at the top of the container and wherein a hanging means from which the I.V. bag system may be suspended during use is provided on said cap means.

21. The I.V. bag system of claim 20 wherein the hanging means is configured so as to be operable only after the medicament has been dispensed into the diluent.

22. The I.V. bag system of claim 17 wherein the cup means is comprised of glass and the plunger means is comprised of rubber.

* * * * *

UNITED STATES PATENT AND TRADEMARK OFFICE

CERTIFICATE OF CORRECTION

PATENT NO. : 4,781,679

DATED : November 1, 1988

INVENTOR(S) : Mark E. Larkin

It is certified that error appears in the above—identified patent and that said Letters Patent is hereby corrected as shown below:

Column 6, line 58: Change "and" to --end--

Signed and Sealed this

Fourth Day of April, 1989

Attest:

DONALD J. QUIGG

*Attesting Officer*

*Commissioner of Patents and Trademarks*